US012527722B2

(12) United States Patent
Wakim et al.

(10) Patent No.: US 12,527,722 B2
(45) Date of Patent: Jan. 20, 2026

(54) SMART MEDICATION HOLDER

(71) Applicant: Bigfoot Biomedical, Inc., Milpitas, CA (US)

(72) Inventors: Michael J. Wakim, Milpitas, CA (US); Rachael Price, Milpitas, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 75 days.

(21) Appl. No.: 18/506,869

(22) Filed: Nov. 10, 2023

(65) Prior Publication Data

US 2024/0156686 A1 May 16, 2024

Related U.S. Application Data

(60) Provisional application No. 63/383,221, filed on Nov. 10, 2022.

(51) Int. Cl.
*B65D 83/04* (2006.01)
*A61J 7/00* (2006.01)
*A61J 7/04* (2006.01)
*G16H 10/60* (2018.01)
*G16H 20/13* (2018.01)

(52) U.S. Cl.
CPC ........... *A61J 7/0069* (2013.01); *A61J 7/0084* (2013.01); *A61J 7/04* (2013.01); *G16H 10/60* (2018.01); *G16H 20/13* (2018.01); *A61J 2200/70* (2013.01)

(58) Field of Classification Search
CPC .. B65D 75/367; B65D 83/0445; A61J 7/0069; A61J 7/0084; A61J 7/04; G16H 10/60; G16H 20/13
USPC .......................... 206/533, 538, 540; 348/143
See application file for complete search history.

(56) References Cited

U.S. PATENT DOCUMENTS 11,759,393 B2 * 9/2023 Zakaria ................. A61J 7/0445 206/531
2013/0195326 A1 * 8/2013 Bear ..................... A61J 7/0084 382/128
2014/0097119 A1 * 4/2014 Zabinski ................ A47B 77/16 206/557
2014/0346068 A1 * 11/2014 Omura ................... B65D 25/06 206/534
2016/0022542 A1 * 1/2016 Lehmann .............. A61J 7/0436 705/2
2016/0074284 A1 * 3/2016 Despa ................... A61J 7/0454 206/534

(Continued)

FOREIGN PATENT DOCUMENTS

RU 43168 U1 1/2005

OTHER PUBLICATIONS

International Search Report and Written Opinion of PCT/US2023/079432, Mar. 27, 2024, 7 pages.

*Primary Examiner* — Luan K Bui
(74) *Attorney, Agent, or Firm* — HSML P.C.

(57) ABSTRACT

A medication holder may include a housing having a top side defining one or more wells, respective wells configured to receive a medication package or medication container; at least one image sensor arranged to capture an image of an exterior of a medication package when a medication package is received in at least one of the one or more wells; and a processor configured to determine information about the exterior of a medication package from one or more images of the exterior of the medication package.

15 Claims, 3 Drawing Sheets

(56) References Cited

U.S. PATENT DOCUMENTS

| | | | | |
|---|---|---|---|---|
| 2016/0354283 | A1 | 12/2016 | Cho et al. | |
| 2018/0289591 | A1 | 10/2018 | French et al. | |
| 2022/0160585 | A1 | 5/2022 | Stein et al. | |
| 2023/0096507 | A1 * | 3/2023 | Wingate, III .......... | G16H 20/13<br>206/528 |
| 2023/0233411 | A1 * | 7/2023 | Knobel ..................... | A61J 1/03<br>206/538 |

* cited by examiner

SMART MEDICATION HOLDER

CROSS-REFERENCE TO RELATED APPLICATION

This application claims the benefit under 35 U.S.C. § 119(e) of U.S. Provisional Patent Application Ser. No. 63/383,221, filed Nov. 10, 2022, the disclosure of which is hereby incorporated herein in its entirety by this reference.

TECHNICAL FIELD

Examples relate generally to assisting with medication adherence. Some examples relate to providing time-relevant information to a patient about when to dose a medication. Some examples relate to a medication holder that provides time-relevant information to a patient about when to dose a medication.

BACKGROUND

Medication nonadherence—when patients do not take their medications as prescribed—is unfortunately fairly common, especially among patients with chronic disease. Examples of typical reasons for nonadherence include forgetfulness; confusion about when to take a prescribed medication, especially if the patient is taking many medications; fear of potential side effects; the cost of the medication; and misunderstandings about the need for the medication. Medication nonadherence can have immediate or long-term health consequences for the patient, and if a healthcare professional does not have an understanding about medication nonadherence, that healthcare professional may needlessly escalate the patient's treatment, resulting in potential harm to the patient, unnecessary work for the healthcare professional, and increased costs overall. Accordingly, there is a need for devices, systems, and methods that assist patients in overcoming medication nonadherence issues and/or that help healthcare professionals understand information about a patient's adherence to prescribed medications.

BRIEF SUMMARY

One or more examples discussed herein may provide time-relevant information to the patient about when to dose a medication. One or more examples may provide medication dosing information to patients, caregivers, or healthcare professionals. Such time-relevant information and medication dosing information may include, as non-limiting examples, time-relevant information and medication dosing information that assists with medication adherence.

One or more examples may assist a patient or caregiver with remembering when to take one or more medications, reduce risk of confusing different medications, or reduce cumbersome human input steps and errors the result therefrom.

BRIEF DESCRIPTION OF THE DRAWINGS

For a detailed understanding of the present disclosure, reference should be made to the following detailed description, taken in conjunction with the accompanying drawings, in which like elements have generally been designated with like numerals, and wherein.

Figure 1:
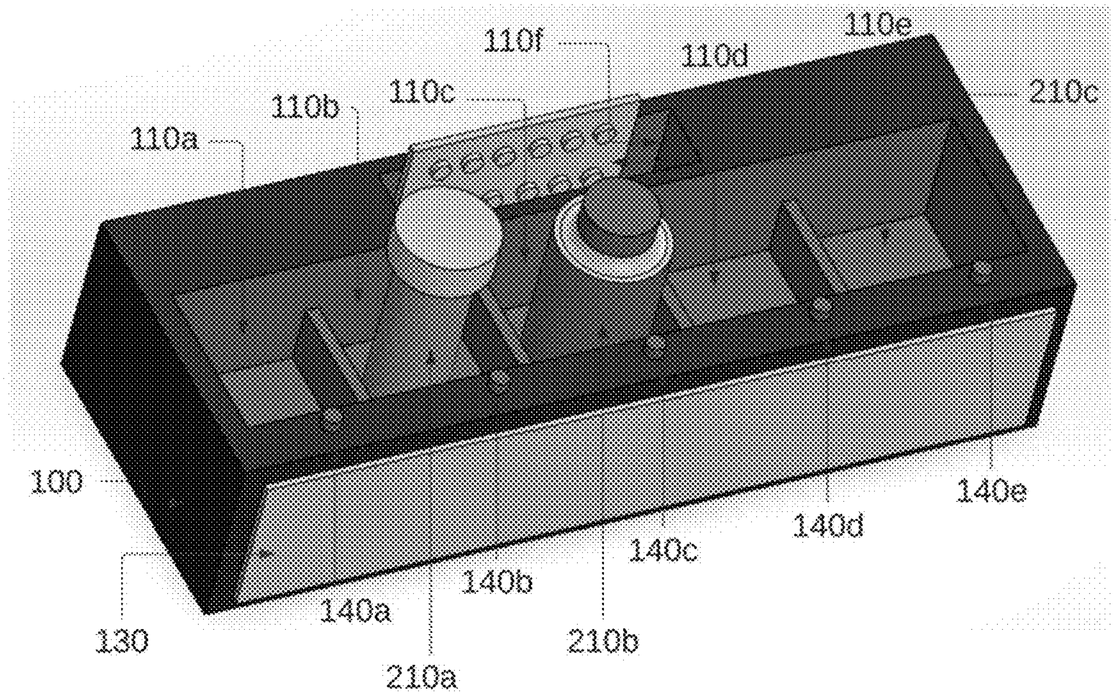
FIG. 1 is a perspective view of a smart medication holder, in accordance with one or more examples.
Figure 2:
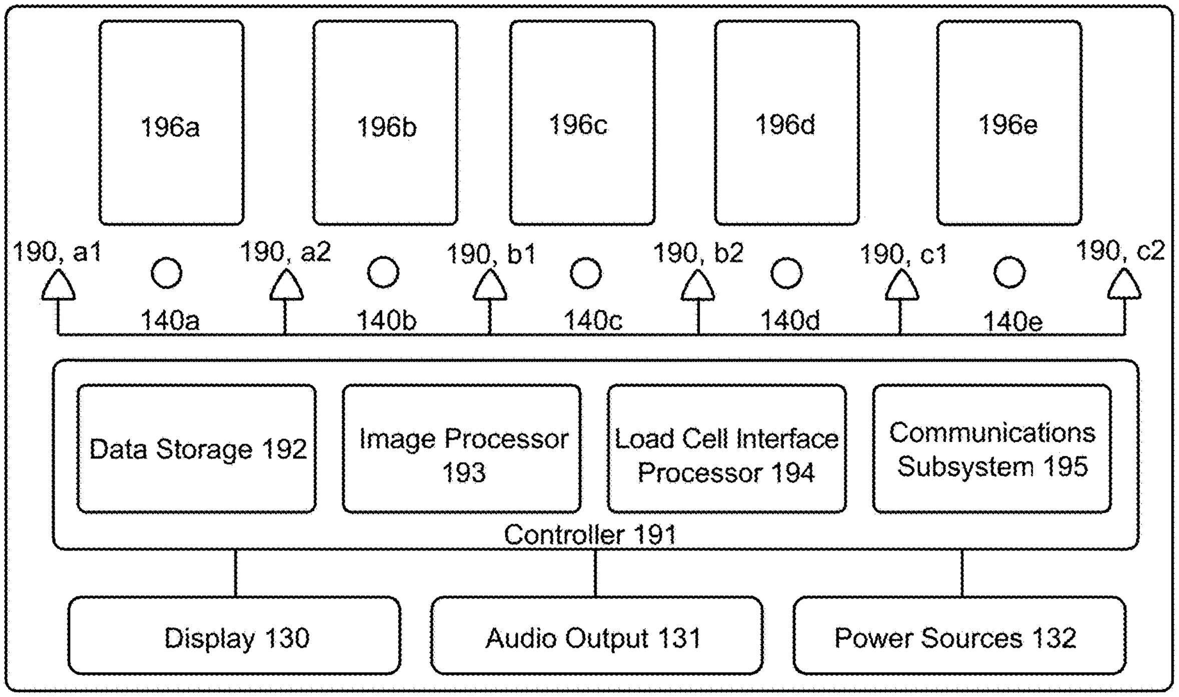
Figure 3:
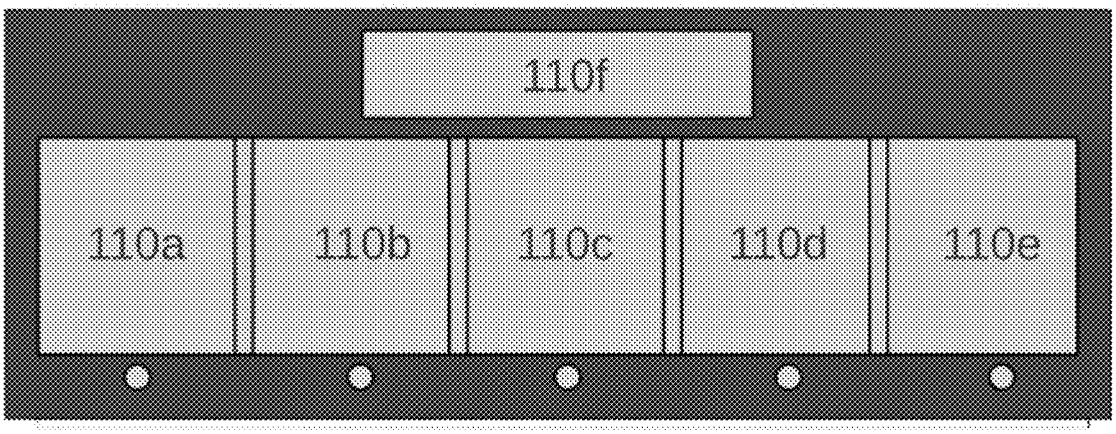
Figure 4:
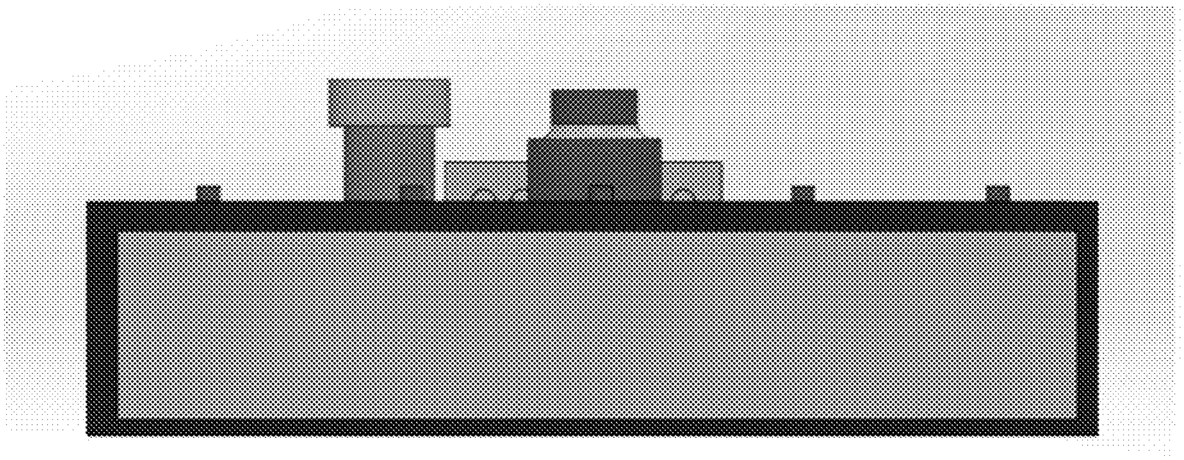
Figure 5:
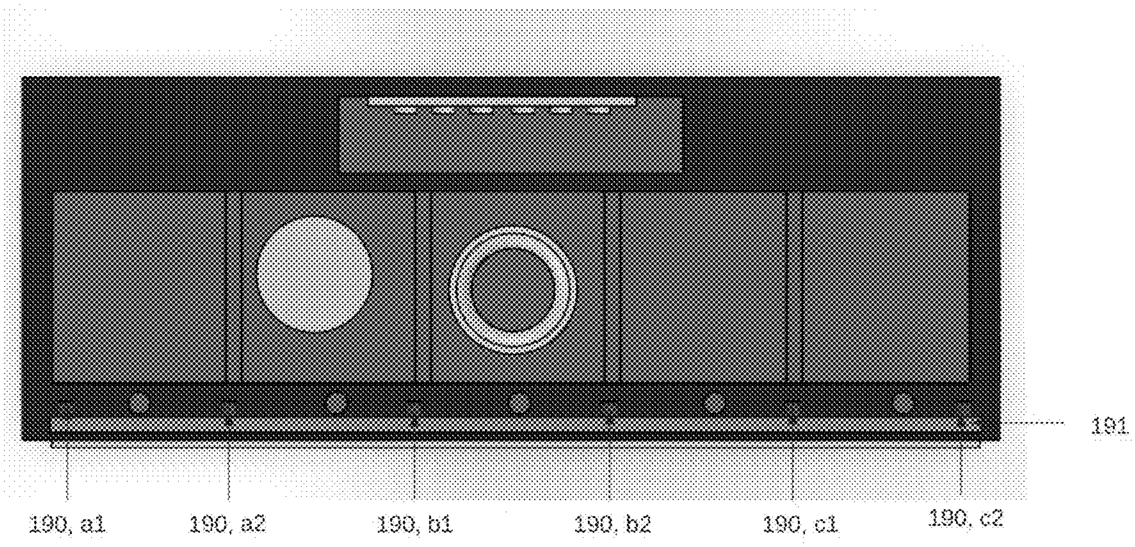

the example smart medication holder depicted by FIG. 1 received various medication packages;

FIG. 2 is a block diagram of internal components of a smart medication holder, in accordance with one or more examples;

FIG. 3 is an exemplary cross-sectional view of medication packages receiving recess (also referred to as "wells") of a smart medication holder;

FIG. 4 is a side view of an exemplary smart medication holder of FIG. 1; and FIG. 5 depicts an exemplary locking mechanism for a platform within a recess of a smart medication holder, in accordance with one or more examples.

DETAILED DESCRIPTION

The illustrations presented herein are not actual views of any smart medication holder, or any component thereof, but are merely idealized representations, which are employed to describe embodiments of the present invention.

As used herein, the singular forms following "a," "an," and "the" are intended to include the plural forms as well, unless the context clearly indicates otherwise.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

As used herein, any relational term, such as "first," "second," "top," "bottom," "upper," "lower," "above," "beneath," "side," "upward," "downward," etc., is used for clarity and convenience in understanding the disclosure and accompanying drawings, and does not connote or depend on any specific preference or order, except where the context clearly indicates otherwise. For example, these terms may refer to an orientation of elements of any smart medication holder when utilized in a conventional manner. Furthermore, these terms may refer to an orientation of elements of any smart medication holder as illustrated in the drawings.

As used herein, the term "substantially" in reference to a given parameter, property, or condition means and includes to a degree that one skilled in the art would understand that the given parameter, property, or condition is met with a small degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter, as well as variations resulting from manufacturing tolerances, etc.).

FIG. 1 is a perspective view of a smart medication container holder 100 (also referred to herein as "medication holder 100"), in accordance with one or more examples. A smart medication holder 100 may include various wells (e.g., multiple wells of similar or different size (dimensions) and shape, without limitation), 110*a*-110*f*, defined by interior walls of medication holder 100 (example interior walls are depicted by FIG. 1 but not labeled). Wells may also be referred to herein as "recesses." Respective wells 110*a*-110*f* are sized and shaped for medication container types. It should be understood that size and shape of respective wells 110*a*-110*f* are a matter of design choice, e.g., based on different medication container types, without limitation. Medication holder 100, and respective wells therein, may be compatible with, but is not limited to, prescription bottles 210*a*, over the counter medication or vitamin bottles 210*b*, and blister packages 210*c*. Medication holder 100 may include, or be configured to include, a variety of different attachments that may optionally connect to the system (e.g., system 200, without limitation) via a connection point or an interface, such as an expansion port, slot, or other physical interface, without limitation. Such different attachments may permit customization of the medication holder 100 for larger, smaller, or unusual container types (e.g., unusual in terms of geometry or shape, without limitation) that may not fit in some or all of wells 110*a*-110*f*. This may include containers for powder medications or supplements, without limitation. The wells 110*a*-110*f* of medication holder 100 are not limited to a singular geometry, size, or shape. The geometry, size, and shape of wells 110*a*-110*f* are not limited to the examples depicted in in FIG. 1 (110*a*, 110*b*, 110*c*, 110*d*, 110*e*, 110*f*). One or more indicators may be located in front of the respective wells (based on the perspective view in FIG. 1) to indicate which medication is to be taken at a predetermined time as shown in FIG. 1 (140*a*, 140*b*, 140*c*, 140*d*, 140*e*). In one or more examples, the number of indicators may be the same or different as the number of wells. In one or more examples, respective indicator lights 140*a*, 140*b*, 140*c*, 140*d*, 140*e* may be light emitting diodes (LEDs) or digital displays controlled by system 200.

FIG. 2 is a block diagram of a system 200 of components (e.g., electronic components, without limitation) of smart electronics for use with, or as a component of, an example medication holder 100. In accordance with one or more examples. In one or more examples, system 200, as shown in FIG. 2, may include a controller 191, indicator lights 140*a*, 140*b*, 140*c*, 140*d*, 140*e*, an audio output 131, a display 130, and power sources 132. The controller 191 may include, but is not limited to, a data storage 192, and a communications subsystem 195, and one or more processors to perform or control various functions or operations of logical blocks, circuits, modules, or components discussed herein (e.g., general purpose processors, application specific integrated circuits (ASICs), digital signal processors (DSPs), logic circuits, including, but not limited to, an image processor 193, a load cell interface processor 194).

Information may be presented to the user, but is not limited to, via a display 130 on the medication holder 100, via a software application executing on a mobile computing device, tablet computer, laptop computer, or the Cloud, without limitation. Various settings for notifications may be presented and controlled via the display 130, a software application on a mobile device, tablet, computing device, tablet computer, laptop computer, or the Cloud, without limitation.

System 200 may include light sources and sensors (e.g., image sensors that utilize a camera, a laser, or a special purpose "reader" (e.g., barcode reader, QR code (quick-response code) or other two or three-dimensional code reader, without limitation), without limitation), that may read the labels (e.g., capture information presented or stored on physical labels, without limitation) on the medication containers. In one or more examples, the light sources may be, but are not limited to, a wide angle light source that diffuses light to ensure the medication bottle labels are illuminated for analysis. In one or more examples, the image sensors may be positioned between one or more of the intersection of the wells. For example, in FIG. 2 ((190, *a*1-*a*2), (190, *b*1-*b*2), (190, *c*1-*c*2)) there are six image sensors positioned for the five wells depicted by FIG. 1. The image sensors 190*a*1, 190*a*2, 190*b*1, 190*b*2, 190*c*1, and 190*c*2 may also be positioned in the front and back of the wells to view all sides of the medication and the label. Medication holder 100 may also include any number of rows of wells, including one row, two rows, or three rows of wells. The number of wells may depend, as a non-limiting example, on specific operating conditions. In examples with multiple rows of wells, medication holder 100 may include respective rows of sensors for respective rows of wells and so may optionally include multiple rows of sensors.

The information collected by the sensors may be processed by the one or more processors (e.g., image information processed by the image processor 193) and may be stored locally in the data storage 192 or stored in the Cloud via the communications subsystem 195. Information collected from a label of a medication container by the sensors may include, but is not limited to, a Unique Device Identifier (UDI), National Drug Code (NDC), a brand, generic, street, or other name of the medication, the name of a patient the medication is prescribed to, the dose amount, and further instructions on what time of day to take and whether to take with food, whether to take on an empty stomach, with or without other medications, and the expiration date, without limitation. In a contemplated operation, respective image sensors 190*a*1, 190*a*2, 190*b*1, 190*b*2, 190*c*1, and 190*c*2 may provide input (e.g., captured image information, without limitation) to the image processor 193, the image processor 193 may process the input to extract output, the output may include information discussed above, and the output may be stored, presented via a display, communicated to a software application or the cloud, or a combination thereof, without limitation.

In one or more examples, a medication holder 100 may include various settings (e.g., customizable or otherwise changeable settings, without limitation). Such settings may be set, as non-limiting examples, at least partially based on a user's preference or a health care professionals' recommendations. These settings may include, but are not limited to, the time and day of notification for different medications, whether for breakfast, lunch, or dinner, the amount of medication in a prescription, the amount of medication to dose, a frequency of dose, a number of doses per day, and further health care professional recommendations such as whether to take with food or on an empty stomach. One or more of the aforementioned settings may be settable e.g., via a user interface (not depicted), or a computing device such as a smart phone. Medication holder 100 may notify a user (e.g., via the indicator lights, display, or a communication to an application on a mobile computing device, without limitation) of unique dosing information (e.g., time sensitive dosing information, user specific dosing information, safety related dosing information, without limitation). Unique dosing information may include, but is not limited to, if they are running low on medications, if their medications are expired, if medications can't be taken together, contraindications (e.g., the medication cannot be taken with alcohol in the system or other medications or types of medications, without limitation), without limitation.

System 200 may also be utilized to enable medication holder 100 to be utilized by more than one user. Respective users may input multiple users into the system 200 and the settings maintained by system 200. Different settings may be input for respective users via a user interface such as display 130 or via a mobile computing device, without limitation.

Alternatively or in addition to the customizable settings discussed above, medication holder 100 and more specifically system 200 may receive indications of additional notification settings such as a color of a light indicator (e.g., an LED of a light indicator, without limitation) should display for respective users, what noise the audio system will sound, without limitation.

In one or more examples, medication holder 100 may monitor the amount of medication in a medication container. The mechanism to monitor the amount of medication may include one or many load cells, such as load cells 196*a*, 196*b*, 196*c*, 196*d*, 196*e* depicted by FIG. 2. (Respective load cells determine the weight of the medication bottle (and contents thereof) and system 200 may determine the difference of the determined weights at predetermined intervals (e.g., predetermined time intervals, without limitation)). In this manner, system 200 may determine one or more changes in amount of medication in a medication container or well. System 200 may, at least partially based on the information about the amount of medication, determine if the user is taking the prescribed dose out of the system. For example, the controller 191 may gather load information a load cell interface processor 194 and store such load information locally in the data storage 192. The controller 191 may, additionally or alternatively to locally storing, send the load information through the communications subsystem to store that load information in the Cloud. This may also allow for the user to be notified when they are running low on a medication and may provide a reminder to refill their medication.

The controller 191 may send various information to: the display 130, the audio output 131, and the indicator lights 140*a*, 140*b*, 140*c*, 140*d*, 140*e*. In one or more examples, the audio content presented via audio output 131 may verbalize dosing information and dosing instructions for a user. The audio output 131 may present audio content to notify the user that it is time to take a medication. Audio content may be customizable, so it is heard and identifiable to the user. System 200 may audibly state information to the user. The audio output 131 may, at least partially responsive to commands from controller 191, audibly state, as non-limiting examples, a user's name, name of the medication, and/other identifying or dosing information.

While not depicted by FIG. 2, system 200 may include a time source or a connection to a time source (e.g., a local clock, a Cloud service, a mobile computing device (such as a mobile phone), without limitation) and use time information from the time source to determine when to capture or present at least the information discussed herein.

The communication subsystems 195 may send information to the Cloud and interact with various Cloud services. The communication subsystems 195 may also receive information from a mobile computing device, the Cloud, without limitation. The received information may include, but is not limited to, a health care professionals' recommendations regarding dosing information and dosing instructions or settings.

A mobile application may be associated with medication holder 100 and utilized on a mobile device, tablet, computer, without limitation. In one or more examples, the mobile application may track multiple dosing information. The mobile application may also include multiple accounts for respective users pertaining to one or more medication holder systems (such as, without limitation, medication holder 100 or other medication holder systems, without imitation). The mobile application may include an interface (e.g., a graphical user interface, without limitation) to adjust and enter customizable settings discussed herein. The mobile application may allow a user to provide (e.g., present a user interface to input, without limitation) additional dosing information regarding medications. The mobile application may also allow a user to provide (e.g., present a user interface to input, without limitation) further dosing information regarding non-prescription medications such as over the counter medications, vitamins, powders, without limitation. This additional dosing information may include what user the medication is for and other unique dosing information.

In one or more examples, medication holder 100 may connect (e.g., electronically communicate with, without limitation) with remote physical monitoring devices or systems. A health care professional may, via a connected remote monitoring system, observe, as non-limiting examples, how often a patient is taking their medication, whether they are taking it at the right time and the right amount, without limitation. Such a remote monitoring system may include a web interface for a healthcare professional to review patient information, such as physiological information or psychological information. Such a web interface may also allow for the healthcare professional to update information remotely to their patient regarding dosing information such as when to take, how much to take, etc.

In one or more examples, a medication holder 100, a remote monitoring system, or both may also connect to physiological data management or capture devices, such as, but not limited to, a scale, heart rate monitoring devices, movement devices, and health informatics applications (e.g., a health informatic application on a mobile phone, in the cloud, without limitation). In one or more examples, a medication holder 100, a remote monitoring system, or both may connect to a scale via a wired or wireless connection (e.g., via a cellular chip, BLUETOOTH® chip, Wi-Fi chip, without limitation). In one or more examples, a medication holder 100, a remote monitoring system, or both may allow for the health care professional to monitor chronic conditions such as obesity, heart disease, without limitation.

In one or more examples, a system that includes medication holder 100 may include a software application for a caregiver. This may allow for a caregiver such as a parent, guardian or loved one to monitor how their child or loved one is taking medications. This information may include if they are taking their medication, how much medication they are taking, and at what time they are taking their medication. The software application for a caregiver may also be utilized on a mobile device, tablet, computer, etc. The software application for a caregiver may also be able to follow multiple users of the system or a singular user.

In one or more examples, medication holder 100 may include one or more safety mechanisms. Such a safety mechanism may be a lid to the medication holder that may optionally include a latching and/or locking mechanism. In one or more examples, a locking mechanism may be activated through a passcode on the system's display or through the mobile application, and so may at least partially be controlled by controller 191. In a contemplated operation, aa user may activate the locking mechanism when they are leaving the room of the medication holder. This may provide a means of limiting access to medications to children or unintended individuals. In one or more examples the lid may be moveable and/or removeable. As a non-limiting example, the lid may be hinged to move and expose the wells.

FIG. 3 depicts an empty smart medication holder 100 of FIG. 1 at top-down perspective view. FIG. 4 depicts a smart medication holder 100 of FIG. 1 at a back-front perspective. FIG. 5 depicts smart medication holder 100 from a top-down perspective.

Those of ordinary skill in the art would understand that information and signals may be represented using any of a variety of different technologies and techniques. Some drawings may illustrate signals as a single signal for clarity of presentation and description. It will be understood by a person of ordinary skill in the art that the signal may represent a bus of signals, wherein the bus may have a variety of bit widths and the present disclosure may be implemented on any number of data signals including a single data signal.

The various illustrative logical blocks, modules, and circuits described in connection with the embodiments disclosed herein may be implemented or performed with a general purpose processor, a special purpose processor, a Digital Signal Processor (DSP), an Integrated Circuit (IC), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor (may also be referred to herein as a host processor or simply a host) may be a microprocessor, but in the alternative, the processor may be any conventional processor, controller, microcontroller, or state machine. A processor may also be implemented as a combination of computing devices, such as a combination of a DSP and a microprocessor, a plurality of microprocessors, one or more microprocessors in conjunction with a DSP core, or any other such configuration. A general-purpose computer including a processor is considered a special-purpose computer while the general-purpose computer executes computing instructions (e.g., software code) related to embodiments of the present disclosure.

The examples may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a thread, a function, a procedure, a subroutine, a subprogram, without limitation. Furthermore, the methods disclosed herein may be implemented in hardware, software, or both. If implemented in software, the functions may be stored or transmitted as one or more instructions or code on computer-readable media. Computer-readable media includes both computer storage media and communication media including any medium that facilitates transfer of a computer program from one place to another.

Any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. In addition, unless stated otherwise, a set of elements may comprise one or more elements.

The examples described herein and illustrated in the accompanying drawings do not limit the scope of the disclosure, which is encompassed by the scope of the appended claims and their legal equivalents. Any equivalents (e.g., equivalent embodiments, without imitation) are within the scope of this disclosure. Indeed, various modifications of the examples or the elements described, in addition to those shown and described herein and illustrated in the accompanying drawings, such as alternate combinations (e.g., alternate useful combinations, without limitation) of the examples or the elements described, will become apparent to those skilled in the art from the description. Such modifications and examples also fall within the scope of the appended claims and equivalents.

What is claimed is:

1. A medication holder configured to store one or more medication packages, the medication holder comprising:

a housing having a top side defining one or more wells, respective wells configured to receive one of the one or more medication packages;

at least one image sensor arranged to capture an image of an exterior of at least one of the one or more medication packages received in at least one of the one or more wells;

a processor configured to determine information about the exterior of at least one of the one or more medication packages from one or more images of the exterior of the at least one of the one or more medication packages; and one or more load cells configured to monitor a weight of at least one of the one or more medication packages received in the one or more wells, wherein the processor is configured to determine a difference of a monitored weight of at least one of the one or more medication packages received in the one or more wells at predetermined intervals.

2. The medication holder of claim 1, wherein the medication holder is configured to detect an insertion or removal of one of the one or more medication packages from at least one of the one or more wells.

3. The medication holder of claim 1, wherein the processor is configured to use optical character recognition to determine at least one of the following: a name of a prescribed patient, a type of medication, a dose amount per tablet or pill, a dosing schedule for the medication, a dose size for the prescribed patient per dose, dosing instructions, and an expiration date of the medication.

4. The medication holder of claim 1, wherein the processor is configured to send one or more images to a remote processor to determine at least one of the following: a name of a prescribed patient, a type of medication, a dose amount per tablet or pill, a dosing schedule for the medication, a dose size for the prescribed patient per dose, dosing instructions, and an expiration date of the medication.

5. The medication holder of claim 1, wherein the processor is configured to provide a prompt to a user to indicate an upcoming, due, or overdue dose.

6. The medication holder of claim 5, wherein the processor is configured to determine a recommended dose timing for at least one of the one or more medication packages received in at least one of the one or more wells.

7. The medication holder of claim 1, wherein interior walls of the medication holder define respective boundaries of the wells.

8. The medication holder of claim 7, wherein the respective interior walls are moveable to change a size and shape of the respective wells.

9. The medication holder of claim 1, comprising a movable lid to cover the one or more wells and assist with retaining contents thereof.

10. The medication holder of claim 9, wherein the movable lid includes a latching mechanism and/or locking mechanism.

11. The medication holder of claim 1, wherein the information determined by the processor includes one or more contraindications of a medication stored in at least one of the one or more medication packages.

12. The medication holder of claim 1, further comprising at least one light source configured to diffuse light such that a label of the one or more medication packages can be illuminated for analysis.

13. A medication container holder, comprising:

a housing having a top side defining one or more wells, respective wells configured to receive one or more medication packages;

a sensor configured to detect whether one of the one or more medication packages is received in a first well;

an indicator configured to provide information to a user about when a dose of a medication is scheduled for administration;

at least one image sensor arranged to capture an image of an exterior of at least one of the one or more medication packages when at least one of the one or more medication packages is received in at least one of the one or more wells;

a processor configured to determine information about the exterior of at least one of the one or more medication packages from one or more images of the exterior of the one or more medication packages; and one or more load cells configured to monitor a weight of at least one of the one or more medication packages received in the one or more wells, wherein the processor is configured to determine a difference of a monitored weight of at least one of the one or more medication packages received in the one or more wells at predetermined intervals.

14. The medication container holder of claim 13, wherein the information determined by the processor includes one or more contraindications of a medication stored in at least one of the one or more medication packages.

15. The medication container holder of claim 13, further comprising at least one light source configured to diffuse light such that a label of the one or more medication packages can be illuminated for analysis.

* * * * *